United States Patent [19]

Thomas et al.

[11] 4,337,858

[45] Jul. 6, 1982

[54] LENS CASE

[75] Inventors: Michael D. Thomas; Francis E. Ryder, both of Arab, Ala.

[73] Assignee: Ryder International Corporation, Arab, Ala.

[21] Appl. No.: 134,742

[22] Filed: Mar. 27, 1980

[51] Int. Cl.³ .............................. B08B 3/04; B08B 3/00
[52] U.S. Cl. ..................................... 206/5.1; 134/137
[58] Field of Search ................. 206/5.1; 220/20.5, 22; 134/166 R, 154, 137

[56] References Cited

U.S. PATENT DOCUMENTS

| 2,944,661 | 7/1960 | Goldstein | 134/137 |
| 3,394,717 | 7/1968 | Hollinger | 134/137 |
| 3,460,552 | 8/1969 | Sturgeon | 206/5.1 X |
| 3,536,082 | 10/1970 | Kolbeck | 206/5.1 X |

FOREIGN PATENT DOCUMENTS 1403667  8/1975  United Kingdom ................ 206/5.1

Primary Examiner—Steven M. Pollard
Attorney, Agent, or Firm—Trexler, Bushnell & Wolters, Ltd.

[57] ABSTRACT

There is disclosed a basic lens case design, which is adapted for use in the storage and sterilization or disinfecting of contact lenses. The lens case design includes shallow, cup-like base and cover section. The base member and cover member include cooperating means for closure and a sealing structure to effect the retention of suitable sterilizing or disinfecting fluid therein. The base member has a partition defining a pair of similar compartments, each for receiving a lens and a quantity of sterilizing or disinfecting solution, the partition having a through opening formed therein permitting the free flow of solution and thereby maintaining substantially equal amounts of the disinfecting solution in the two pockets. In addition, the partition is spaced from this top surface a selected distance which is sufficient to prevent any pinching or damage to a lens.

11 Claims, 11 Drawing Figures

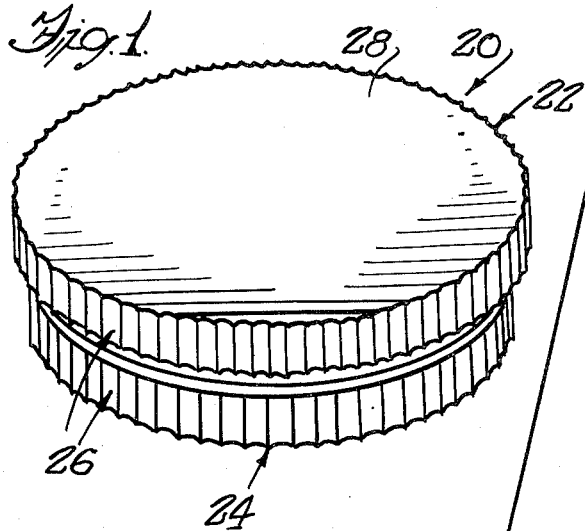
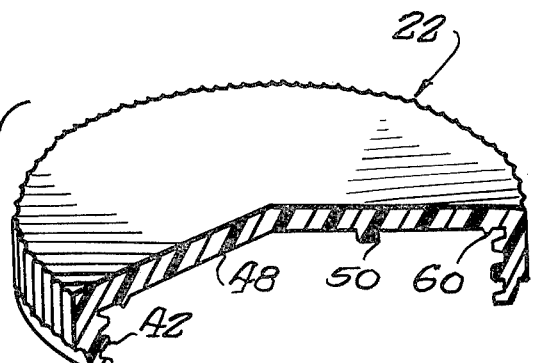
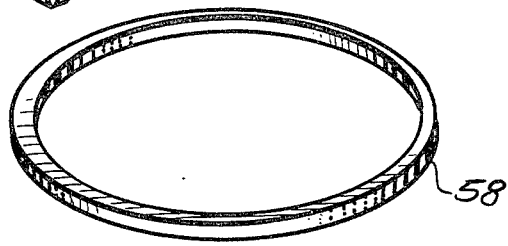
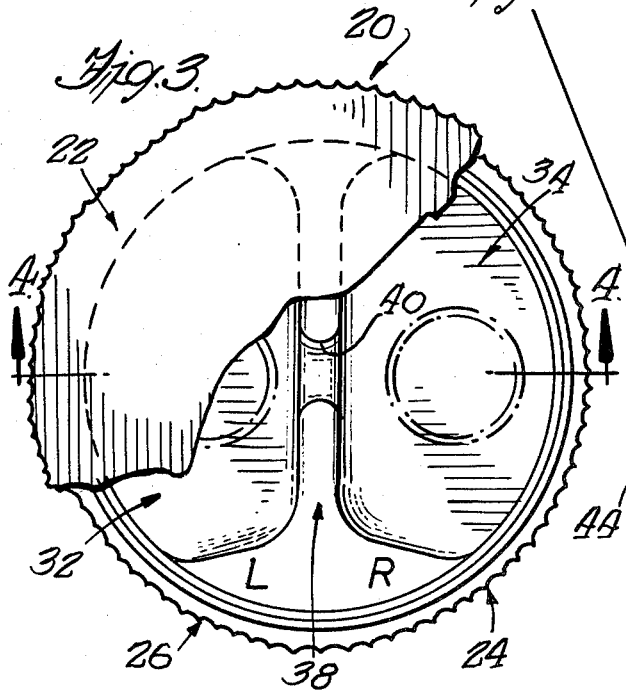
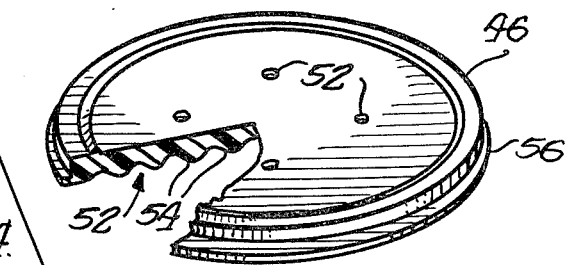
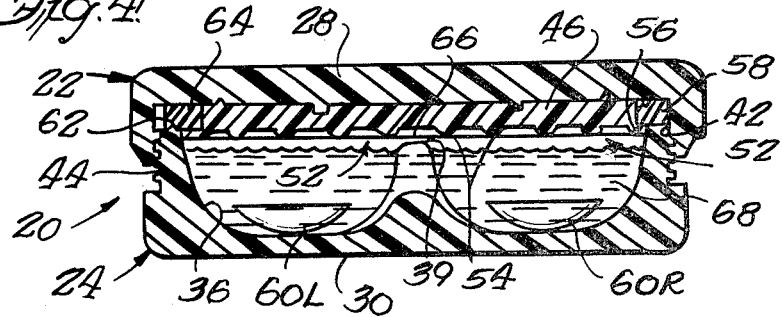

ic
LENS CASE

BACKGROUND OF THE INVENTION

This invention relates to a lens case for storing a pair of contact lenses, and more specifically, a case that can be used for storage as well as the disinfecting and/or sterilizing of said contact lenses.

The first contact lens developed were of the "hard" variety and disinfecting and/or sterilization of these was not a critical procedure, since this type of lens did not provide a suitable medium for bacteria growth. With the advent of newer "soft" contact lens certain problems have evolved, which were not heretofore encountered with respect to cleaning and sterilization procedure employed with hard lenses. Specifically, the soft contact lenses are generally manufactured from a hydrophilic plastic material, which is relatively porous such that it will absorb water, and become soft and pliable. The porous nature of this material provides a medium for bacteria growth, which can lead to eye infections, and thus necessitates relatively frequent, i.e. daily, disinfecting or sterilization, to prevent the accumulation of undesirable bacteria.

A number of sterilization methods have been developed for use with the soft contact lenses. A first one of these methods involves immersion of the lenses in a disinfecting solution, usually a saline solution, and heating of the solution to a temperature sufficient to destroy the bacteria that might be present. A second method that has been developed employs a chemical process to destroy bacteria and achieve sterilization. With regard to the heating method of sterilization this, in turn, may be accomplished by either a "wet heat" process or a more recently developed "dry heat" process. In the former process, the lenses are first placed in a case containing a saline solution and this case is then placed in a vessel of water which is brought to the boiling point, heat transfer to the sterilizing case and lenses in the solution therein being accomplished by the surrounding water. As can be appreciated, the water will be heated only to its boiling point, and as such the actual temperature advanced within the lens case will not exceed that of the water, and due to heat loss will be somewhat lower. In the second or "dry heat" method, the lenses are placed within a sealed or airtight case and the saline solution added, whereupon the case is positioned in direct contact with a dry heating element, such that there is direct application of heat to a surface of the case or container and hence to the sterilizing solution and lenses therein. With this method and the use of a sealed vessel, the solution can be superheated, that is heated to a level above the normal, atmospheric boiling point of the disinfecting solution.

The prior art includes a number of lens cases which were developed primarily for use in the "wet heat" process, for example as shown in U.S. Pat. Nos. 3,770,113; 3,977,517; 4,009,777. While these prior art cases work well in wet heat applications, and can be used in dry heat disinfecting process, they are possessed of certain shortcomings when used with the dry heat type of sterilization. In contrast, the lens cases of this invention, as will become apparent from the following description, are particularly well adapted for use in the dry heat sterilization process. Moreover, these lens cases include a number of advantageous features which render them useful for the storage of either hard or soft contact lenses, or for use in the wet heat type of sterilization process, as well.

More specifically, the lens cases of this invention are adapted to accommodate the lenses in a pair of similar pockets disposed in side-by-side relation in a relatively shallow flat casing structure. This casing structure, which includes a base member and a cover member, has at least one exterior flat surface area configured for broad surface-to-surface engagement with a heating element to facilitate and enhance heat transfer. A pair of similar pockets or compartments are defined by a partition in the base member of the case. This partition is provided with a suitable aperture or trough for assuring that a substantially equal amount of disinfecting solution will flow into the respective pockets, without regard for the point of introduction of the solution. The trough or aperture is sized, however, to preclude passage of a lens from one pocket to the other. Further, in a first embodiment the partition is of a height, such that when the cover is closed, its upper edge is closely spaced relative to the confronting inner surface of the cover member. As such should a lens inadvertently be interposed between the partition and inner cover surface, the lens will not be impinged upon or "pinched" to the extent that it will be damaged. However, this spacing is selected such that transmigration of a lens from one pocket to the other during rotation of the cover, is precluded. More specifically, the lenses are extremely pliable and in the wetted condition there is a possibility that they may adhere to the cover. In the event this occurs, rotation of the cover pursuant to opening may result in displacement of the lens from its assigned pocket, or the inadvertent depositing of a lens in the wrong pocket. With the first design, the partition effects a wiping action which will dislodge any lens adhered to the cover member. Moreover, the interior surfaces forming the pockets are generally curvilinear in cross section, substantially avoiding any recesses, sharp corners or the like where residue from the saline or other disinfecting solutions might otherwise accumulate. As will be more fully described hereinbelow, the interior surface of the cover member is provided with an irregular surface to prevent or discourage adherence of a lens thereto. In a second embodiment of the invention, a screen or apertured lid is pivotally connected to the base and overlies the partition and the pockets to maintain the lenses in proper location.

It will be appreciated that the foregoing structural considerations substantially prevent the respective lenses for the right eye and the left eye being confused or reversed, as the lenses will remain in the pockets in which they are initially placed. As a further matter in this regard, suitable indicia such as letters R and L are preferably included at suitable positions with respect to the two pockets, as a further indication of the lenses to be contained therein.

BRIEF DESCRIPTION OF THE DRAWINGS

The foregoing, as well as other objects, features and advantages of the present invention will become more readily apparent upon a reading of the following detailed description taken in conjunction with the accompanying drawings, in which:

FIG. 1 is a perspective view of the exterior portion of a lens case constructed in accordance with the present invention;

FIG. 2 is an exploded perspective view, partially broken away, of the lens case of FIG. 1;

FIG. 3 is a top view, partially broken away of the lens case of FIGS. 1 and 2 with a pair of lenses shown in phantom;

FIG. 4 is a sectional view, taken generally along the line 4—4 of FIG. 3;

DETAILED DESCRIPTION OF THE ILLUSTRATED EMBODIMENT

Figure 5:
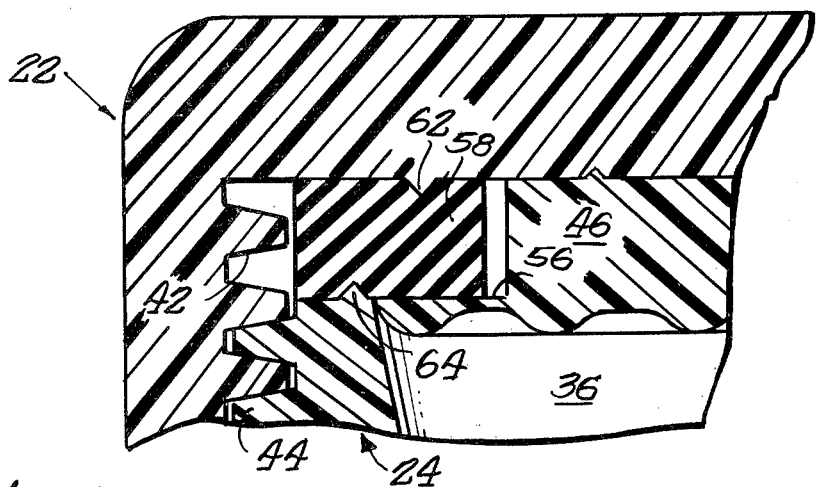
FIG. 5 is an enlarged sectional view of a portion of the section 4—4 illustrated in FIG. 4.

A first embodiment of a lens case in accordance with the invention and designated generally 20, is illustrated in FIG. 1 fully closed, so that only the exterior portion thereof is visible. In this regard, it will be seen that the lens case 20 includes a cover member 22 and a base member 24. Both of these members are generally circular, disc-like members in their exterior surface appearance, and are provided with knurled peripheral surfaces, as indicated generally by reference numeral 26, to facilitate gripping and handling thereof. Both the cover member 22 and base member 24 have generally flat surfaces 28 and 30, which form the top and bottom, respectively, of the lens case 20. These flat surfaces minimize the overall height or thickness of the closed lens case structure 20, while presenting a broad bottom surface 30. The bottom surface 30, as best viewed in FIG. 4, also advantageously cooperates with the heating element of the unit (not shown) with which the case is to be used. In this regard, an exemplary structure of one such sterilizer or heating unit is illustrated and described in the copending application of Michael D. Thomas, Ser. No. 877,671, filed Feb. 14, 1978, entitled "Lens Holder."

Reference is now invited to FIG. 2 wherein the lens case 20 is illustrated in exploded perspective view, and partially broken away, to illustrate further advantageous features of the present invention. Both the base portion 24 and cover portion 22 are seen to be of a relatively shallow cup-like configuration, with the base portion 24 including a pair of adjacent compartments, wells or pockets, designated 32 and 34, respectively, each for receiving one of a pair of contact lenses. These compartments or pockets 32 and 34 are defined by the interior surface 36 of the base member 24, together with a partition 38. This partition 38 is provided with at least one through aperture or trough 40, whose structure and function will be more fully discussed hereinbelow. With reference also to FIG. 4, it will be seen that the interior wall surfaces 36 of the base member 24, as well as the walls of the partition 38, are generally curvilinear surfaces, thereby avoiding any sharp corners, recesses, or the like wherein residue from the disinfecting solution might otherwise accumulate.

Figure 8:
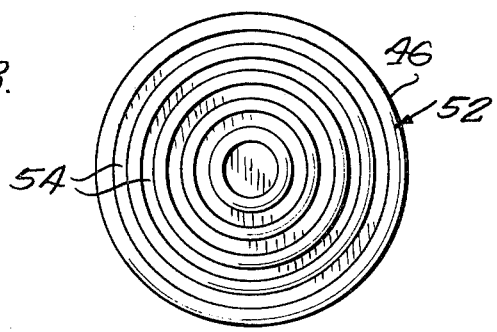
FIG. 8 is a plan view of an insert forming an interior top surface portion of the cover member of the lens case of this invention.

With continued reference to FIG. 2, the cover member 22 and the base member 24 are provided with mating, peripherally formed threaded portions 42, 44, which cooperate to permit joining and closure of the lens case 20. In the illustrated embodiment, the cover 22 is of a specific construction. In this regard, a disc-like insert member 46 interfits with and is assembled to the inner surface 48 of the cover member 22 to provide a suitable interior top surface 52 of the lens case 20, and, as will be discussed, retain the sealing ring 58. The inner surface 48 of cover member 22 includes a number of lugs or projections 50, which interfit with suitable slots or apertures 52 in the insert member 46 for alignment and retention purposes. Further, the insert 46 includes an annular weld bead 47 to facilitate attachment of the insert 46 to cover member 22 by an ultra-sonic welding process, with the weld thus produced serving to seal the space between element 22 and insert 46. As an additional feature, the insert member 46 is provided with an irregular surface, designated generally 52 which forms the interior top surface of the lens case 20. More particularly and with reference to FIGS. 4 and 8, this irregular surface 52 is seen to comprise a plurality of annular, concentric raised rings 54. These raised rings 54 advantageously avoid a suction cup-like adhesion of a contact lens, such as lenses 60L and 60R illustrated in FIG. 4, as might otherwise occur with a substantially flat interior top surface.

The insert member 46, referring back to FIG. 2, is further seen to include an annular, peripherally disposed flange portion 56, which when said insert 46 is assembled with the cover member 22 serves to confine and hold an annular sealing ring 58 in position about the periphery of the surface 48 thereof. This annular sealing ring 58 is preferably formed of a resilient material, so as to effect sealing engagement with cooperating portions of the base 24. As best viewed in FIG. 4 and FIG. 5, a substantial portion of the annular sealing ring 58 is exposed generally radially outwardly of the flange portion 56 of the insert 46. Cooperating sealing means are provided in the base member 24 and cover member 22 in the form of respective raised annular ridges or beads 62, 64. Consequently, upon threaded engagement between the base member and cover member 22 and relative rotation thereof to effect closure of the lens case 20, the respective annular ridges or beads 62 and 64 impinge upon the flexible sealing ring 58, to effect sealing thereof. Advantageously, this sealing not only retains saline or other disinfecting solution 68 but also allows a degree of pressure build up, which is thereafter maintained, during heating of the lens case 20, thus enabling the solution 68 to be heated above its normal, atmospheric boiling point.

Figure 6:
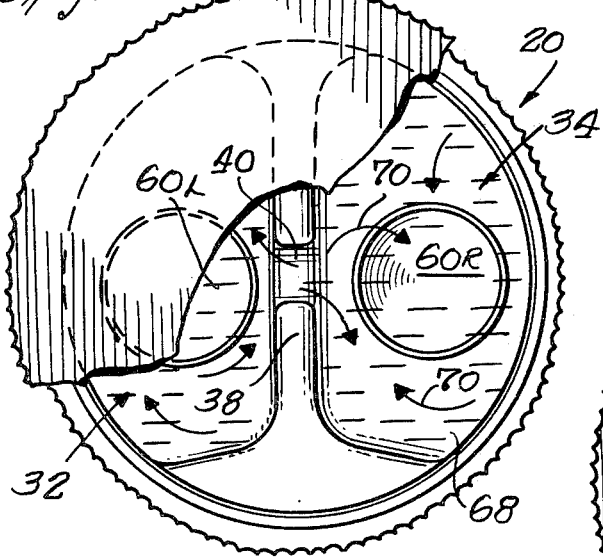
FIG. 6 and FIG. 7 are top views, partially broken away, and similar to FIG. 3, illustrating further facets of the operation of the lens case of this invention.

As a further advantage, with respect to this sealing action, it will be noted that the relatively large external diameters of the base and cover members 22, 24, together with the knurled edge surfaces 26 thereof permit a relatively high degree of torque to be manually applied. Consequently, during rotation and threaded engagement in closing, this torque assures a good seal between the sealing ring 58 and cooperating surfaces, as described. Consideration is now directed to the partition member 38 and through aperture 40 and their respective functions. With reference to FIG. 4 and FIG. 6, it will be seen that the aperture 40 is of such a size as to permit the flow of the disinfecting solution 68 between the compartments or pockets 32 and 34, but is not so large as to permit the lenses 60L or 60R to move therethrough. Advantageously, substantially equal amounts of fluid 68 may be maintained in both compartments 32 and 34 substantially without regard to the point of actual filling thereof. As a further advantageous feature, it will be noted that with respect to the lenses 60R, 60L, the pockets 32 and 34 are of sufficient size to accommodate a volume of solution sufficient to emerse the lenses totally, or as is generally considered necessary for proper sterilization.

Referring still to the partition member 38, when the lens case is closed, and as best viewed in FIG. 4, the partition 38 is spaced a distance 66 from the interior top surface 52 of cover 22 presented thereto by the insert member 46. This spacing is such as to substantially prevent damage or "pinching" of the soft lens 60R or 60L, during closure of the lens case 20, should a lens 60R or 60L inadvertently be interposed between the upper surface 39 of the partition 38 and facing, interior top surface 52. However, this spacing, similar to the size of the opening 40 is sufficiently close as to preclude transmigration or shifting of the lenses 60R and 60L between their respective pockets 32, 34, once the lens case 20 is closed.

With reference to the foregoing features, a further advantage of the invention will be considered. It will be recalled that it is desired to provide a relatively flat case, with the lenses carried in side-by-side pockets, to enhance heating. With this design, a possibility exists that a lens 60R or 60L may adhere to the cover 22 at some point in the sterilization processes. Accordingly, as the cover 22 is rotated pursuant to opening the lens 60R or 60L will be moved out of register with its associated pocket 32 or 34. As a result, upon opening, a user may find both lenses adhered to the cover 22, with no way of determining which is for the right eye, and which is for the left eye. Further, there is also the possibility that the lens 60R or 60L may become dislodged from the cover when in register with the wrong pocket. In this instance the user will find both lenses 60R or 60L in the same pocket, again with no way easily to determine which is for the left eye and which is for the right eye. Advantageously, the structure of the lens case 20, as thus far described, is such as to substantially prevent confusion or interchanging of the lenses 60R and 60L, as discussed above.

Figure 7:
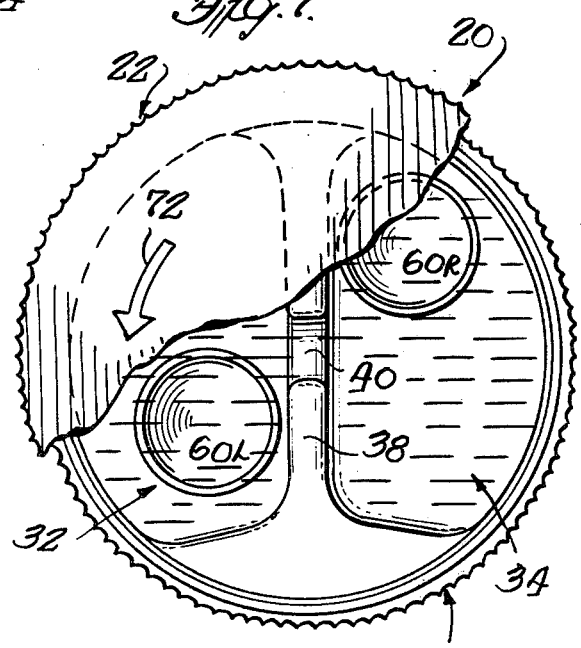

In this regard, the described spacing between the partition 38 and facing interior surface 52 facilitates maintaining the lenses 60R and 60L in their respective pockets. Specifically, and as best viewed in FIG. 7, should a lens 60R or 60L adhere to the interior surface 52 or should the lens case 20 be inverted so that the lenses 60L and 60R are resting on this interior surface 52, the following action will occur upon opening or closing of the case 20, which is accomplished, as described, by relative rotation of the cover member 22. For example, opening the closed case 20 may be accomplished by rotation of cover 22 in the direction indicated by arrow 72. Consequently, one or both lenses 60R, 60L if adhering to or resting upon the interior surface 52, will tend to be carried by the cover 22 in the same direction, viz, as indicated by arrow 72. However, upon the lens 60R and/or 60L encountering the partition 38, said lens will be precluded from further advancement in this direction, as the spacing 66 between the partition and the cover will not permit the lens to pass. As such there is provided a wiping action that serves to maintain the lenses 60R and 60L in their respective pockets 32 and 34. As a further matter, the rounded or curvilinear form of the pockets 32 and 34 serve to enhance this wiping action.

Figure 9:
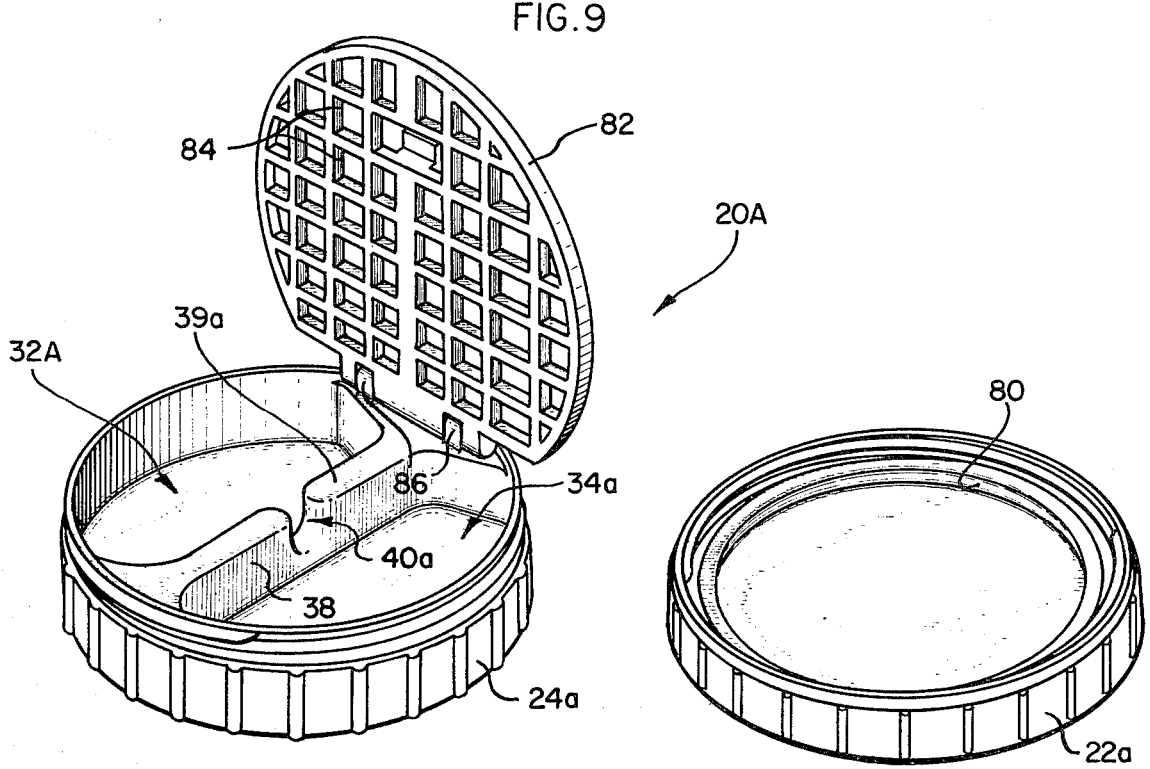
FIG. 9 is a perspective view of a modified form of the invention, and illustrates the lens case base and cover in the open condition, with the screen on the base pivoted to the open position.
Figure 10:
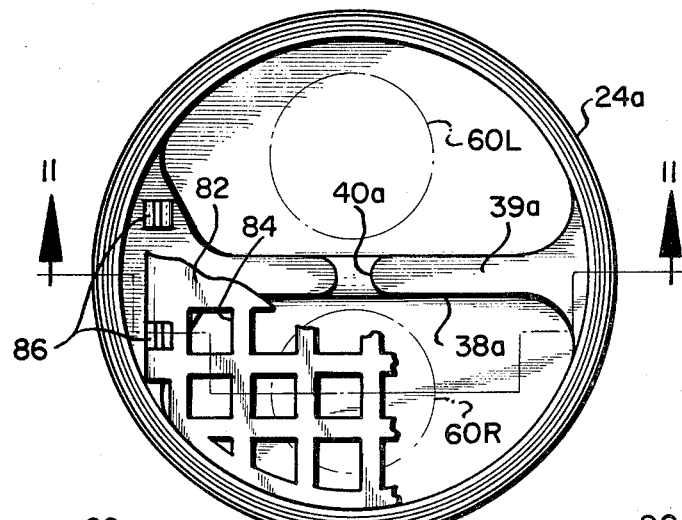
FIG. 10 is a top plan view of the lens case base of FIG. 9 with the screen pivoted to the closed position and partially broken away.
Figure 11:
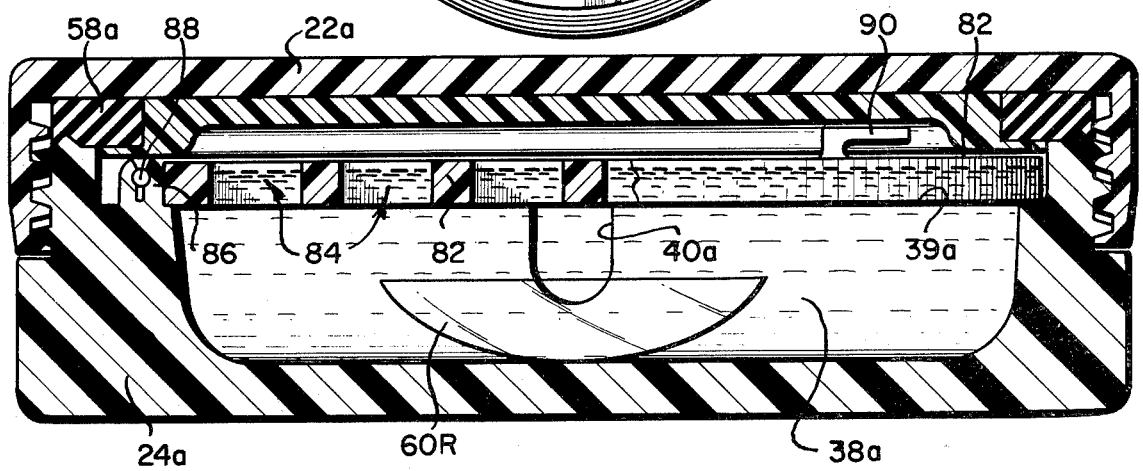
FIG. 11 is a sectional view through an assembled cover and base, taken generally along the line 11—11 of FIG. 10, and with the screen broken away for purposes of illustration.

In FIGS. 9-11 a second embodiment of the invention is illustrated, and designed generally 20a. The case 20a is shown open in FIG. 9, and includes a cover 22a and a base 24a, said cover and base being provided with interengagable thread means for effecting closure of the case. The cover 22a is similar to the cover 22 as discussed previously, except that the raised rings 54 have been eliminated, and in place thereof the inner surface of the cover includes a circular depression 80, for a purpose to be discussed with respect to FIG. 11. The base member 24a includes a pair of pockets 32a and 34a defined at least partially by a central partition 38a. The partition 38a has an opening 40a formed therein, and a substantially flat upper surface 39a.

The base 24a differs from that as discussed above previously in the addition of a pivotally mounted lid or screen 82. More specifically the screen or lid 82 is sized to fit within the inner rim of the base 24a and includes a plurality of apertures 84 formed therein. In order to effect pivotal mounting of the screen 82, the upper surface of the partition 38a includes a pair of upstanding, bifracted bosses 86 (see FIG. 11) into which are disposed a corresponding pair of rod-like pintle segments 88 formed on the screen 82. This engagement is effected by a snap-fit type of action and permits the screen 82 to pivot between the open condition of FIG. 9 and the closed position of FIGS. 10 and 11.

Referring now to FIGS. 10 and 11 it can be seen that when closed the screen 82 overlies the respective pockets 32a and 34a, and is disposed within the perimeter of the base and below the upper surface thereof. Further, as best seen in FIG. 11 the screen includes a finger grip or lug 90 to facilitate opening thereof, preparatory to removal of a set of lenses 60L and 60R from the case 20a.

Looking now to FIG. 11, the case is shown in the closed condition. In this regard, it should be noted that the cover 22a includes a gasket 58a engaged by a rim portion of the base 24a to seal the interior space of the case. Further, in the closed position the circular recess 80 in the cover serves to accommodate the finger lug 90, and also provides a space wherein disinfecting solution can pass from one pocket to the other. This flow of solution is also enhanced by the opening 40a in the partition 38a and the aperture 84 in said screen 82. In the closed condition, the screen 82 overlies the pockets 32a and 34a and serves to prevent the lenses from being displaced from a desired pocket, with the reticulated nature of the screen 82 not impeding free flow of the disinfecting solution.

Thus, with the embodiment 20a the lenses are positively retained in the respective pockets by the screen 82, but free flow of the disinfecting solution between the respective pockets is not precluded. Further in this regard, it should be noted that two paths are provided for movement of solution between pockets 32a and 34a, the first through the opening 40a, the second, over the partition 38a via the apertures 84 in the screen 82. Thus, any fluid motion or hydraulic movement occurring during carrying or transportation of the lens case 20a is accommodated by both paths. As such, the hydraulic forces tending to force or move a lens through opening 40a into the wrong pocket are reduced, due to the presence of the second fluid path over the partition 38a.

While the lens cases of the present invention have been discussed and described herein with specific reference to use in the disinfecting of soft lenses, it will be appreciated that the utility thereof is not limited to soft lenses. On the contrary, from the foregoing, it is believed clear and intended that the described cases 20 and 20a may be useful in the storing or carrying of contact lenses of the hard variety. In this regard, the case, due to its described sealing features, may readily be used to store or carry lenses in a suitable cleaning or wetting solution, as well. Moreover, the lens cases are equally useful in conjunction with the discussed "wet heat" method of sterilization as well as the described "dry heat" method, or chemical disinfecting processes.

While specific embodiments have been illustrated and described herein, it will be understood that the invention is not limited thereto. It is intended that such alternatives, changes or modifications as might occur to those skilled in the art also be covered, insofar as such alternatives, modifications or changes fall within the spirit and scope of the appended claims.

The invention is claimed as follows:

1. A lens case, comprising in combination: a base member and a cover member, said base and cover members having cooperating joining and closing means for selectively joining said base and cover members and thereby closing the lens case, means on said base member including partition means, defining a pair of adjacent pockets, each pocket for receiving a single lens and a quantity of lens disinfecting solution, aperture means in said partition means for permitting said solution to flow between the pockets to maintain substantially equal amounts of said solution therein, said partition means being spaced apart from said cover member, when the lens case is being closed, a sufficient distance for substantially preventing damage to a lens inadvertently located over the partition during said joining and said closing, while substantially preventing transmigration of a lens from one pocket to the other, in the event said lens may adhere to the cover and the cover subsequently rotated as would occur during removal of the cover member after disinfecting of the lenses.

2. A lens case according to claim 1 further including cooperating sealing means on said base member and on said cover member for substantially sealing the lens case when closed so as to allow a build up and retention of pressure therein in response to heating.

3. A lens case according to claim 1 further including interior top surface means on said cover for substantially preventing adhesion of a lens thereto.

4. A lens case according to claim 1 wherein said base member has a substantially flat outer surface of sufficient area to cooperate with a heating element for promoting heat transfer therebetween.

5. A lens case according to claim 1 wherein said pockets are substantially free of sharp corners, small recesses, and the like where residue build up from said cleaning solution might occur.

6. A lens case, comprising in combination: a base member and a cover member, said base and cover members having cooperating joining and closing means for selectively joining said base and cover members and thereby closing the lens case, sealing means for sealing the interior space upon closing of the lens case, means on said base member including partition means, defining a pair of adjacent pockets, each pocket for receiving a single lens and a quantity of lens disinfecting solution, aperture means in said partition means for permitting said solution to flow between the pockets to maintain substantially equal amounts of said solution therein, said partition being spaced from said cover member, when the lens case is in the closed condition, said spacing being sufficient to substantially prevent damaging to a lens inadvertently located over the partition during closing, and said partition further preventing transmigration of a lens between said pockets in the event said lens may adhere to the cover and move therewith as the cover is rotated.

7. A lens case according to claim 6 wherein said cover member includes an irregular top surface facing said base member for substantially preventing adhesion of said lenses to said interior top surface of said cover member.

8. A lens case according to claim 7, wherein said lens case further includes an insert member, said insert member forming said interior top surface of said cover member.

9. A lens case according to claim 8 wherein said insert member has a substantially annular flange for positioning and holding said annular sealing ring with respect to said cover member, while leaving a substantial portion of said sealing ring exposed for cooperating with the raised surface of the base member.

10. A lens case, comprising in combination: a base member and a cover member, said base and cover members having cooperating joining and closing means for selectively joining said base and cover members and thereby closing the lens case, sealing means for sealing the interior space upon closing of the lens case, means on said base member including partition means, defining a pair of adjacent pockets, each pocket for receiving a single lens and a quantity of lens disinfecting solution, aperture means in said partition means for permitting said solution to flow between the pockets to maintain substantially equal amounts of said solution therein, said partition including an upper surface which is spaced a selected distance from the interior top surface of the cover when said case is in the closed condition, said spacing being such that said interior top surface cooperates with said partition, during rotation of said cover as may occur during opening to effect a wiping action with respect to a lens which may have adhered to said interior top surface, thus substantially preventing such an adhered lens from being carried from its intended pocket to the adjacent pocket.

11. A lens case according to claim 10 wherein said interior top surface of the cover member includes a plurality of irregularities to reduce the instances of adherence thereto by a lens, and most particularly to prevent adherence thereto by a suction effect or the like.

* * * * *